(12) United States Patent
Vancamberg et al.

(10) Patent No.: US 10,070,835 B2
(45) Date of Patent: Sep. 11, 2018

(54) X-RAY IMAGING METHOD AND APPARATUS USING POSITIONING ASSEMBLIES HAVING MULTIPLE DEGREES OF FREEDOM

(71) Applicant: GENERAL ELECTRIC COMPANY, Schenectady, NY (US)

(72) Inventors: Laurence Vancamberg, Saint Germain en Laye (FR); Serge Louis Wilfrid Muller, Guyancourt (FR); Razvan Gabriel Iordache, Paris (FR); Aurélie Boudier, Bois d'Arcy (FR)

(73) Assignee: General Electric Company, Schenectady, NY (US)

( * ) Notice: Subject to any disclaimer, the term of this patent is extended or adjusted under 35 U.S.C. 154(b) by 304 days.

(21) Appl. No.: 14/984,865

(22) Filed: Dec. 30, 2015

(65) Prior Publication Data
US 2016/0183899 A1 Jun. 30, 2016

(30) Foreign Application Priority Data

Dec. 31, 2014 (GB) .................................. 1423378.7
Dec. 31, 2014 (GB) .................................. 1423395.1

(51) Int. Cl.
*A61B 6/04* (2006.01)
*B25J 9/16* (2006.01)
(Continued)

(52) U.S. Cl.
CPC .......... *A61B 6/4458* (2013.01); *A61B 6/0457* (2013.01); *A61B 6/4476* (2013.01);
(Continued)

(58) Field of Classification Search
CPC ........... A61B 6/00; A61B 6/04; A61B 6/0407; A61B 6/0414; A61B 6/0457; A61B 6/405;
(Continued)

(56) References Cited

U.S. PATENT DOCUMENTS 4,894,855 A  1/1990 Kresse
6,435,715 B1  8/2002 Betz et al.
(Continued)

FOREIGN PATENT DOCUMENTS

EP  2637594 A2  9/2013
WO  2012065175 A2  5/2012

OTHER PUBLICATIONS

Combined Search and Exam Report for corresponding GB Appln. No. 1423395.1, dated Jun. 25, 2015, 8 pages.
(Continued)

*Primary Examiner* — Anastasia Midkiff
(74) *Attorney, Agent, or Firm* — GE Global Patent Operation; Marc A. Vivenzio

(57) ABSTRACT

A device and a related mammography method employing the device are described. The device comprises an x-ray source, an x-ray detector placed under a support plate for supporting an object and arranged to detect the x-rays coming from the x-ray source after they have passed through the object, and a positioning assembly with an arm having multiple degrees of freedom which is a collaborative robot for positioning the x-ray source with respect to the support plate. A method for performing an imaging procedure, which includes placing an object of interest on the support plate; moving the x-ray source relative to the object of interest along a non-planar trajectory to avoid collision with the object; and activating the x-ray source and the x-ray detector so as to detect the x-rays coming from the x-ray source after
(Continued)

they have passed through the object, thus obtaining a set of x-ray images.

19 Claims, 15 Drawing Sheets

(51) Int. Cl.
*A61B 6/00* (2006.01)
*A61B 90/50* (2016.01)
*A61B 34/37* (2016.01)
*B25J 9/00* (2006.01)
*A61N 5/10* (2006.01)
*B25J 9/06* (2006.01)
*A61B 6/02* (2006.01)
*A61B 6/10* (2006.01)
*A61B 6/12* (2006.01)

(52) U.S. Cl.
CPC .............. *A61B 6/502* (2013.01); *A61B 34/37* (2016.02); *A61B 90/50* (2016.02); *A61N 5/1083* (2013.01); *B25J 9/0087* (2013.01); *B25J 9/1682* (2013.01); *A61B 6/025* (2013.01); *A61B 6/0407* (2013.01); *A61B 6/0414* (2013.01); *A61B 6/102* (2013.01); *A61B 6/12* (2013.01); *A61B 6/4429* (2013.01); *A61B 6/587* (2013.01); *B25J 9/0084* (2013.01); *B25J 9/06* (2013.01); *G01N 2223/321* (2013.01); *Y10S 901/06* (2013.01); *Y10S 901/16* (2013.01)

(58) Field of Classification Search
CPC ....... A61B 6/44; A61B 6/4405; A61B 6/4411; A61B 6/4429; A61B 6/4453; A61B 6/4458; A61B 6/4476; A61B 6/48; A61B 6/50; A61B 6/502; A61B 6/547; A61B 6/587–6/589; A61B 90/50; A61B 2560/00; A61B 2560/04; A61B 2560/0443; A61B 34/00; A61B 34/20; A61B 34/30; A61B 34/32; A61B 34/37; A61B 2034/254; G01N 2223/00; G01N 2223/30; G01N 2223/308; G01N 2223/321; H05G 1/00; H05G 1/02; A61N 5/10; A61N 5/1083; G06T 1/00; G06T 1/0007; G06T 1/0014; B25J 9/00; B25J 9/0009; B25J 9/0084; B25J 9/0087; B25J 9/0096; B25J 9/06; B25J 9/08; B25J 9/16; B25J 9/1628; B25J 9/1643; B25J 9/1679; B25J 9/1682; B25J 19/066; Y10S 901/00; Y10S 901/01; Y10S 901/02; Y10S 901/06; Y10S 901/08; Y10S 901/09; Y10S 901/14; Y10S 901/15; Y10S 901/16; Y10S 901/17; Y10S 901/18; Y10S 901/27; Y10S 901/41; Y10S 901/50
See application file for complete search history.

(56) References Cited

U.S. PATENT DOCUMENTS

| | | | |
|---|---|---|---|
| 2004/0109529 A1* | 6/2004 | Eberhard | A61B 6/025 378/23 |
| 2007/0071168 A1* | 3/2007 | Allison | A61N 5/1031 378/65 |
| 2009/0175562 A1* | 7/2009 | Pan | A61B 6/032 382/312 |
| 2010/0098214 A1 | 4/2010 | Star-Lack et al. | |
| 2011/0276179 A1 | 11/2011 | Banks et al. | |
| 2012/0029694 A1 | 2/2012 | Muller | |
| 2012/0035462 A1* | 2/2012 | Maurer, Jr. | A61B 6/5247 600/411 |
| 2013/0268120 A1 | 10/2013 | Grygorowicz et al. | |
| 2014/0277740 A1 | 9/2014 | Adelman | |

OTHER PUBLICATIONS

Combined Search and Exam Report for corresponding GB Appln. No. 1423378.7, dated Jun. 24, 2015, 9 pages.

* cited by examiner

X-RAY IMAGING METHOD AND APPARATUS USING POSITIONING ASSEMBLIES HAVING MULTIPLE DEGREES OF FREEDOM

CROSS-REFERENCE TO RELATED APPLICATIONS

This patent application claims foreign priority benefits under 35 U.S.C. § 119 to United Kingdom Patent Application No. 1423395.1, filed Dec. 31, 2014, and United Kingdom Patent Application No. 1423378.7 filed Dec. 31, 2014, which are hereby incorporated by reference in their entireties.

BACKGROUND

The present disclosure relates to the field of medical apparatuses and medical examination methods. More particularly, the present disclosure relates to a method and an apparatus for performing an imaging procedure of an object of interest, in particular mammography.

Breast cancer is a prolific cause of life threatening disease that affects millions worldwide. Because early detection greatly improves survival rates, screening methods, such as mammography, have been established to detect malignant lesions as early as possible, resulting in earlier diagnosis and treatment.

Mammography devices, also referred as mammographs, conventionally comprise at least one x-ray source and a console which is arranged opposite said source and intended to receive and support the patient's breast. This console integrates a detector for detecting the x-rays after they have passed through the patient's breast (array of sensors, x-ray sensitive film cassette, etc.) and is associated with a breast compression paddle which is designed to compress the breast against the console when images are being taken. The x-ray source is supported by a mechanical arm of the mammograph, while the x-ray detector is placed under the console. The arm and the console are movable relative to one another and are mechanically coupled.

The mammograph, in order to perform the examination, has to move the x-ray source above the breast so as to acquire the x-ray images and it can move it only along a predetermined path (linear or arc-shaped) defined by the architecture of the mammograph itself. The trajectories performed by the arm are planar.

A physician can also perform the examination, who, in order to perform the examination, has to move the arm above the breast so as to acquire the x-ray images and he can move it step-by-step by pressing different buttons provided on it, each button making the arm move in a predefined direction and/or orientation. When the arm has to be removed from above the x-ray detector so as to let the physician reach the patient's breast, a parking button has to be pressed, thus moving the arm to predefined parking positions.

The mammographs can be further provided with devices for an assisted manipulation of an instrument, such as for example an echographic probe, which the physician may want to use to conduct an additional examination over an area in which there is a possible lesion. However the physician, in order to use such devices, has to localize the lesion to be evaluated by mentally "superimposing" the image acquired by the mammograph over the breast. This requires a lot of efforts and often leads to imprecise localization of the lesion, which may be particularly detrimental.

In addition to the above, the mammographs can also be provided with an apparatus for performing the breast biopsy called biopsy positioner. Such positioner is an auxiliary device fixed, in a manner per se known, to the mammograph, to be used to perform a breast biopsy.

Collaborative robot or "cobot" are moreover well known in the art. A cobot makes possible a direct physical collaboration between a person and a computer controlled manipulator. Cobots may take a number of configurations common to conventional robots. In place of the actuators that move standard robots, cobots use variable transmission elements whose transmission ratio is adjustable under computer control by use of small steering motors. Cobots guide, redirect or steer motions that originate with the human operator. Thus, both the cobot and the human operator apply forces on a common object, which may be for example a tool.

Cobots are used in medical applications, for example applied to devices for performing a biopsy. However, in the medical field cobots are used only for small tools, which are light and easy to move, due to the difficulty in applying cobots design to big devices.

SUMMARY

The embodiments described herein are directed to methods and apparatuses for performing an imaging procedure of an object of interest, in particular a mammography (e.g. a method for performing a mammography examination or procedure) which solves the problems and disadvantages described herein and found in the background art. This can be achieved by the features as defined by the independent claim. Further enhancements are characterized in the dependent claims.

In one aspect, the present disclosure is directed to a mammography device comprising an x-ray source, an x-ray detector placed under a breast support plate for supporting a patient's breast and arranged to detect the x-rays coming from the x-ray generator after they have passed through the patient's breast, and a positioning assembly for positioning the x-ray source with respect to the breast support plate, wherein the positioning assembly comprises an arm having multiple degrees of freedom, said arm being a collaborative robot.

In another aspect of the present disclosure, the arm comprises a plurality of arm portions pivotally connected each other in respective joints, so that each arm portion can rotate with respect to its adjacent arm portions.

In another aspect of the present disclosure, the arm comprises a plurality of arm portions connected each other in respective joints, so that each arm portion can translate with respect to its adjacent arm portions.

In another aspect of the present disclosure, the device further comprises a mobile platform to which the arm is fixed. In another aspect of the embodiment, the arm is supported by a column having at least a vertical guide in which the arm slides along a vertical direction z. In another aspect of the present embodiment, the column also moves along a non-vertical direction z. In another aspect of the present disclosure, the device further comprises at least one supporting element for supporting the breast support plate and the detector. In another aspect of the present disclosure, the at least one supporting element is mechanically decoupled from the arm. In another aspect of the present disclosure, the device further comprises an auxiliary arm arranged to cooperate with the x-ray source and the x-ray detector for performing a breast imaging, said arm being a robot or a cobot. In another aspect of the present disclosure, the at least one supporting element is a robot or a cobot.

In another aspect, the present disclosure is directed to a method for performing mammography by a device comprising an x-ray source, an x-ray detector placed under a breast support plate for supporting a patient's breast and arranged to detect the x-rays coming from the x-ray source after they have passed through the patient's breast, and a positioning assembly for positioning the x-ray source with respect to the breast support plate comprising a collaborative robot arm, wherein the method comprises:

placing a patient's breast on the breast support plate;

placing the x-ray source in a first position by moving arm portions of the arm through mechanical joints connecting such arm portions, said arm being controlled so as to obtain collaborative guides and/or redirection of the motions.

In another aspect, in the method of the present disclosure the first position is a parking position or an initial position of an imaging trajectory. In another aspect of the present disclosure, the method further comprises moving an auxiliary robot or cobot arm to help to perform an additional examination. In another aspect of the present disclosure, the method further comprises moving at least one robot or cobot supporting element supporting the breast support plate.

In one aspect, the present disclosure is directed to a method for performing an imaging procedure by an imaging device comprising an x-ray source, an x-ray detector placed under a support plate for supporting an object of interest and arranged to detect the x-rays coming from the x-ray source after they have passed through the object of interest, and a positioning assembly for positioning the x-ray source with respect to the support plate comprising an arm. The method comprises placing an object of interest on the support plate, moving the x-ray source relative with the object of interest along a non-planar trajectory and activating the x-ray source and the x-ray detector so as to detect the x-rays coming from the x-ray source after they have passed through the object of interest, thus obtaining a set of x-ray images.

In another aspect of the present disclosure, the non-planar trajectory extends in a tridimensional space and not lies in a plane, such trajectory having at least a starting point, a next first intermediate point, a next second intermediate point and a next ending point non-planar.

In another aspect of the present disclosure, the x-ray source is moved by rotating and/or translating arm portions of the arm through mechanical joints connecting such arm portions to be controlled, so as to obtain collaborative guides and/or redirection of the motions of the x-ray source.

In another aspect of the present disclosure, the x-ray source is moved along a non-planar trajectory so as to avoid collision with an interventional device associated to the imaging device. In another aspect of the present disclosure, an interventional device is moved along a non-planar trajectory above the object of interest so as to avoid collision between the interventional device and the x-ray source. In another aspect of the present disclosure, the x-ray source is moved along a non-planar trajectory computed by taking into account the environment, and/or the patient position, and/or the biopsy device position, and/or the auxiliary arm position and/or a priori/pre-exam. In another aspect of the present disclosure, x-ray source is dynamically moved along a non-planar trajectory computed by taking into account the environment, and/or the patient position, and/or the biopsy device position, and/or the auxiliary arm position and/or a priori/pre-exam and/or per-exam information.

In another embodiment the present embodiment is directed to an imaging device for acquiring images of an object of interest, comprising an x-ray source and an x-ray detector placed under a support plate for supporting an object of interest and arranged to detect the x-rays coming from the x-ray source after they have passed through object of interest, wherein the x-ray source is movable relative to the object of interest along a non-planar trajectory between an initial position and an ending position.

In another aspect of the present disclosure, the x-ray source is movable relative to the object of interest along a non-planar trajectory extending in a tridimensional space and not lying in a plane, such trajectory having a starting point, a next first intermediate point, a next second intermediate point and a next ending point, each portion of the trajectory between two consecutive points being non-planar.

In another aspect of the present disclosure, the imaging device further comprises an arm supporting the x-ray source and wherein the x-ray source is movable by rotating and/or translating arm portions through mechanical joints connecting such arm portions, so as to obtain collaborative guides and/or redirection of the motions of the x-ray source. In another aspect of the present disclosure, the x-ray source is movable along a non-planar trajectory so as to avoid collision with an interventional device associated to the imaging device.

At least one of the above embodiments provides one or more solutions to the problems and disadvantages of the background art. One advantage that may be realized in the practice of some embodiments of the described mammography device is that easy displacement of the gantry can be obtained, and free work space around the breast support can be gained. In addition, optimized screening, diagnostic or interventional breast procedures can be performed. Another advantage that may be realized in the practice of some embodiments of the described method for performing an imaging procedure such as mammography is that easy displacement of the x-ray source can be obtained and an optimized screening, diagnostic or interventional breast procedures can be performed. Other technical advantages of the present disclosure will be readily apparent to one skilled in the art from the following description and claims. Various embodiments of the present application may obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate exemplary embodiments of the disclosure and serve to explain, by way of example, the principles of the disclosure.

DETAILED DESCRIPTION

A problem with the common methods for performing an imaging procedure of an object of interest such as mammography is that the x-ray source can be moved only along a predetermined trajectory because the console is mechanically linked to the arm and because the number of degrees of freedom is limited. This limited set of planar trajectories is not optimal and limits artefacts corrections possibilities. It also causes ergonomic problems for the patient as she has to adapt her position to the system to avoid collision between the x-ray source and herself. It also prevents the physician from easily accessing the breast.

A further problem is that, when using the mammograph with this limited set of trajectories, for performing a breast biopsy, guided by stereotaxy or digital breast tomosynthesis, the biopsy positioner is fixed relatively to the detector, thus resulting in two limitations: some images cannot be acquired because of collision risk between x-ray source and biopsy device and images are partially unusable because the biopsy device itself hides a too big portion of the x-ray detector. In addition, the trajectory is the same as for standard mammography and it is not adapted to this configuration.

Yet another problem with the common mammography devices is that the physician has to press many buttons to move the arm in the desired position when performing the examination, thus requiring time to complete each examination. Another problem is that, when parked, the arm cannot be completely pushed away from the detector because the number of parking positions is limited, and the console is mechanically linked to the arm, thus preventing the physician from easily accessing the breast. In addition, as the biopsy device is above the detector, there is a risk of collision between the x-ray source and the biopsy device, thus forbidding some image acquisition.

Accordingly, there is the need to improve methods for performing imaging procedures such as mammography and to improve the mammography device to increase patient comfort and enable physicians to perform more precise examinations by moving the mammograph arm along a safer and optimal path above the patient's breast allowing. There is also a need to improve the mammography device so that the physician can perform a quicker and more precise examination by moving faster the arm above the patient's breast. These improvements would allow a physician to perform additional interventional steps such as a biopsy in a more comfortable way.

Figure 1:
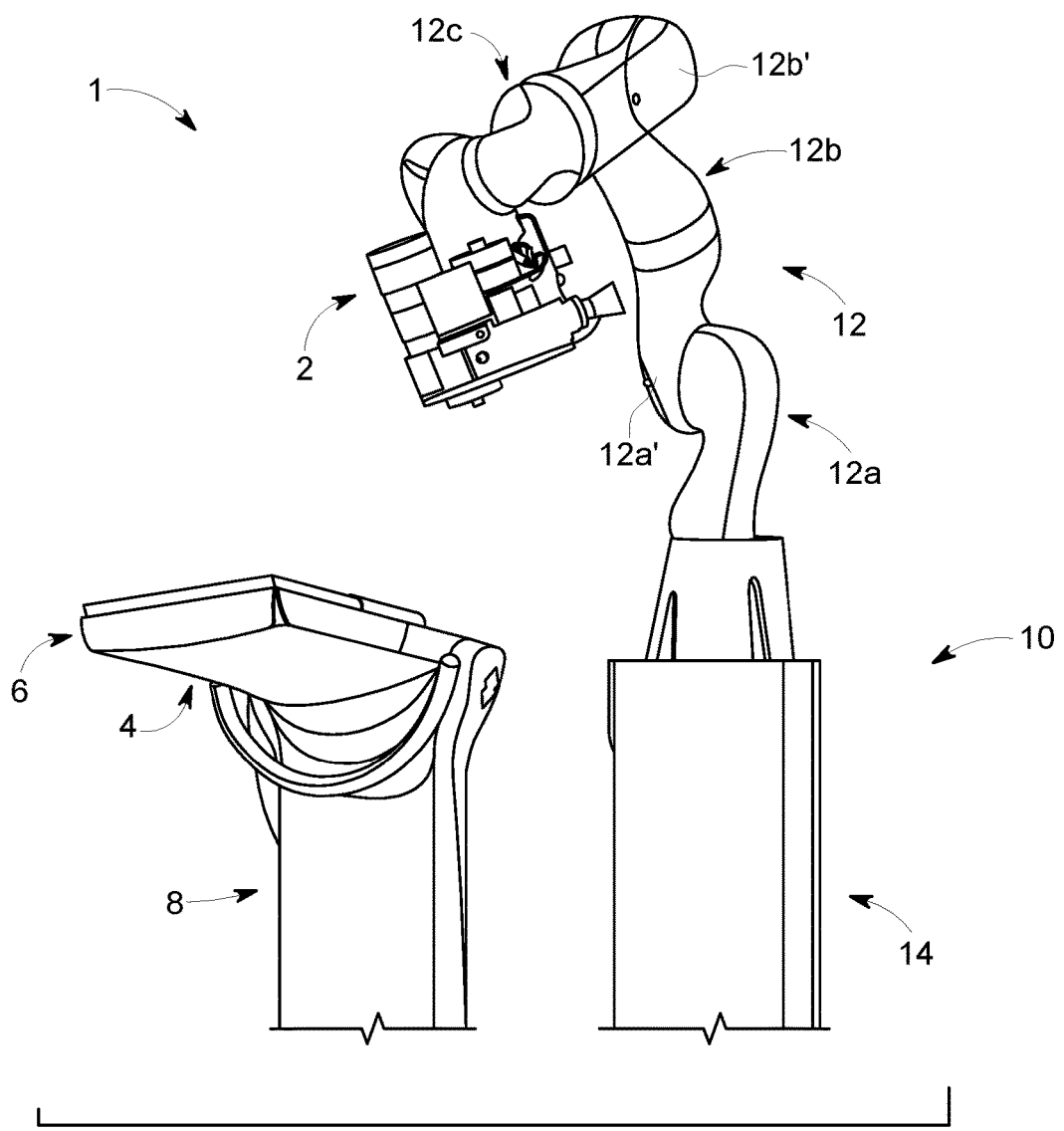
FIG. 1 is a perspective view of a mammography device according to an exemplary embodiment.

With reference first to FIG. 1, an imaging device for performing an imaging procedure such as mammography (e.g. a mammography method used, for example, to conduct a breast examination or another x-ray imaging procedure) according to an exemplary embodiment of the method is generally indicated by reference numeral 1. The device 1 generally comprises an x-ray source 2, an x-ray detector 4 placed under a support plate 6 supported by a supporting element 8, and a positioning assembly 10 for positioning the x-ray source 2 with respect to the support plate 6.

The support plate 6 is arranged to receive and support an object of interest, in particular a patient's breast; the x-ray detector 4 is arranged to detect the x-rays coming from the x-ray source 2 after they have passed through the patient's breast. The device 1 further comprises, in a manner per se known, a breast compression paddle (not shown in the figures) which is designed to compress the breast against the breast support plate when images are being taken.

The positioning assembly 10 comprises an arm 12 supported by a base 14, said arm 12 being decoupled from the x-ray detector 4 and having multiple degrees of freedom so that it can be easily moved in any desired direction above the object of interest. The arm 12 may comprise a plurality of arm portions 12a, 12b, 12c pivotally connected each other in respective joints 12a', 12b', so that each arm portion 12a, 12b, 12c can rotate with respect to its adjacent ones. Alternatively, the arm portions 12a, 12b, 12c are connected to each other with other mechanical joints so that each arm portion 12a, 12b, 12c can translate with respect to its adjacent ones. Alternatively, the arm portions 12a, 12b, 12c can both rotate and translate relative to each other. In at least one aspect of the present description, when referring to the motion of the arm portions 12a, 12b and 12c, it is meant both translation and rotation of them, and any other combination of such movements. The supporting element 8 may be either mechanically coupled or decoupled to the arm 12.

The arm 12 is a collaborative robot (cobot) which can be moved in a co-manipulated mode. This cobot is a computer-controlled robotic apparatus arranged to assist the physician by guiding and/or redirecting motions initiated by him/her. The cobot is therefore intended to physically interact with the physician in a predefined workspace and it includes for example at least a plurality of force sensors in each joint 12a', 12b', motors analysis units and/or sensitive surfaces. The cobot compensates for the gravity forces applied by the x-ray source 2 and enables the physician to manipulate the arm 12 easily. Alternatively, the arm 12 is a robot controlled by a computer.

The arm 12 can be moved independently from the support plate 6 and this allows the arm 12 to perform non-planar trajectories with respect to the x-ray detector 4. In the present description the term non-planar shall mean trajectories extending in a tridimensional space and not necessarily lying in a plane. The x-ray source trajectories can be determined by the knowledge of the patient position and/or the environment around the patient herself, in order to avoid obstacles in the work space of the device 1. The trajectories can be also computed based on a priori or pre-exam or per-exam information on the object to image.

Figure 2:
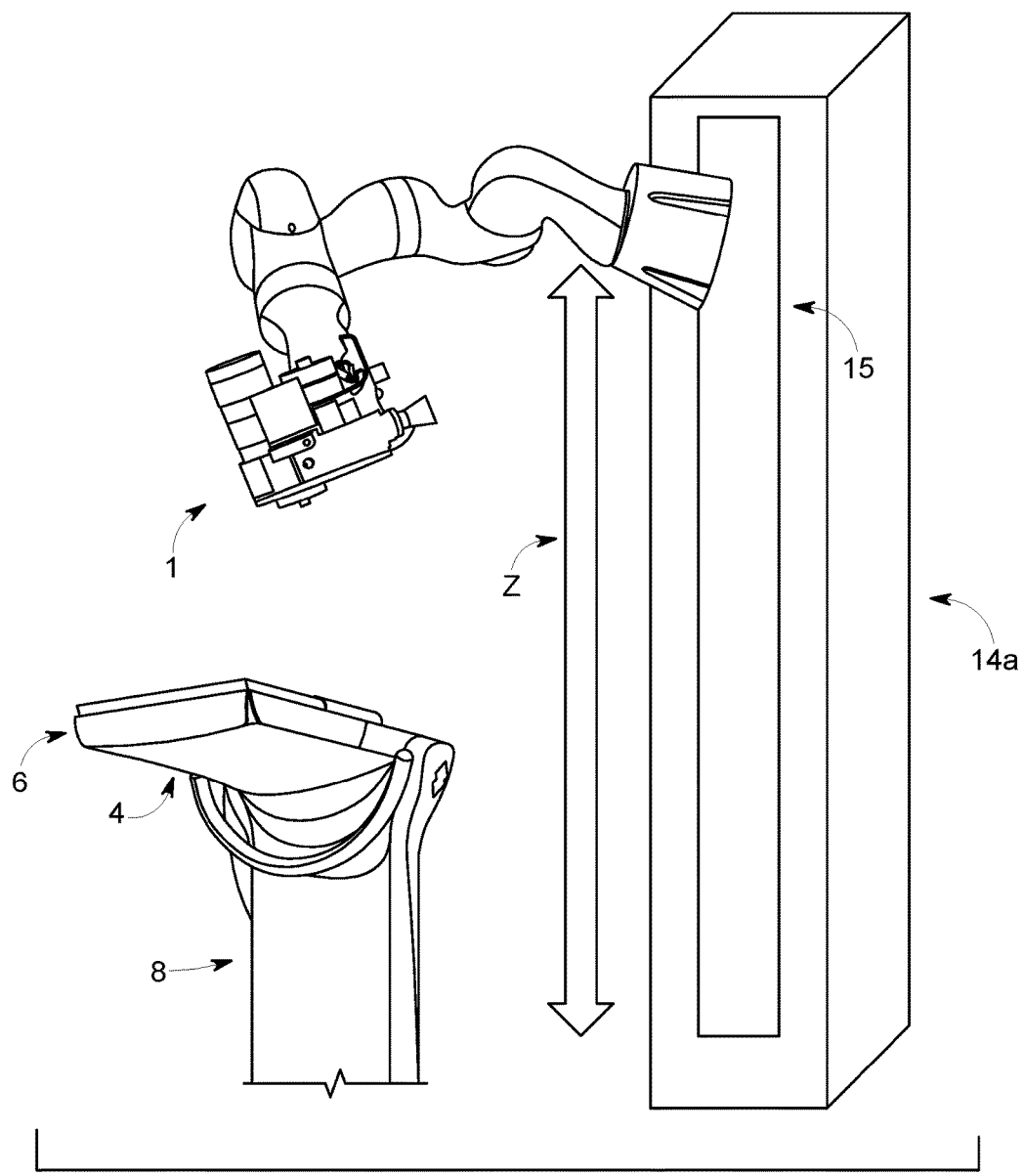
FIG. 2 is a perspective view of a mammography device according to another exemplary embodiment.

In FIG. 2 is shown a perspective view of a mammography device according to another exemplary embodiment wherein the base 14 is replaced with a column 14a having at least vertical guide 15 in which the arm 12 slides along a vertical direction z. Alternatively, the column 14a may also move in another non vertical direction.

Figure 3:
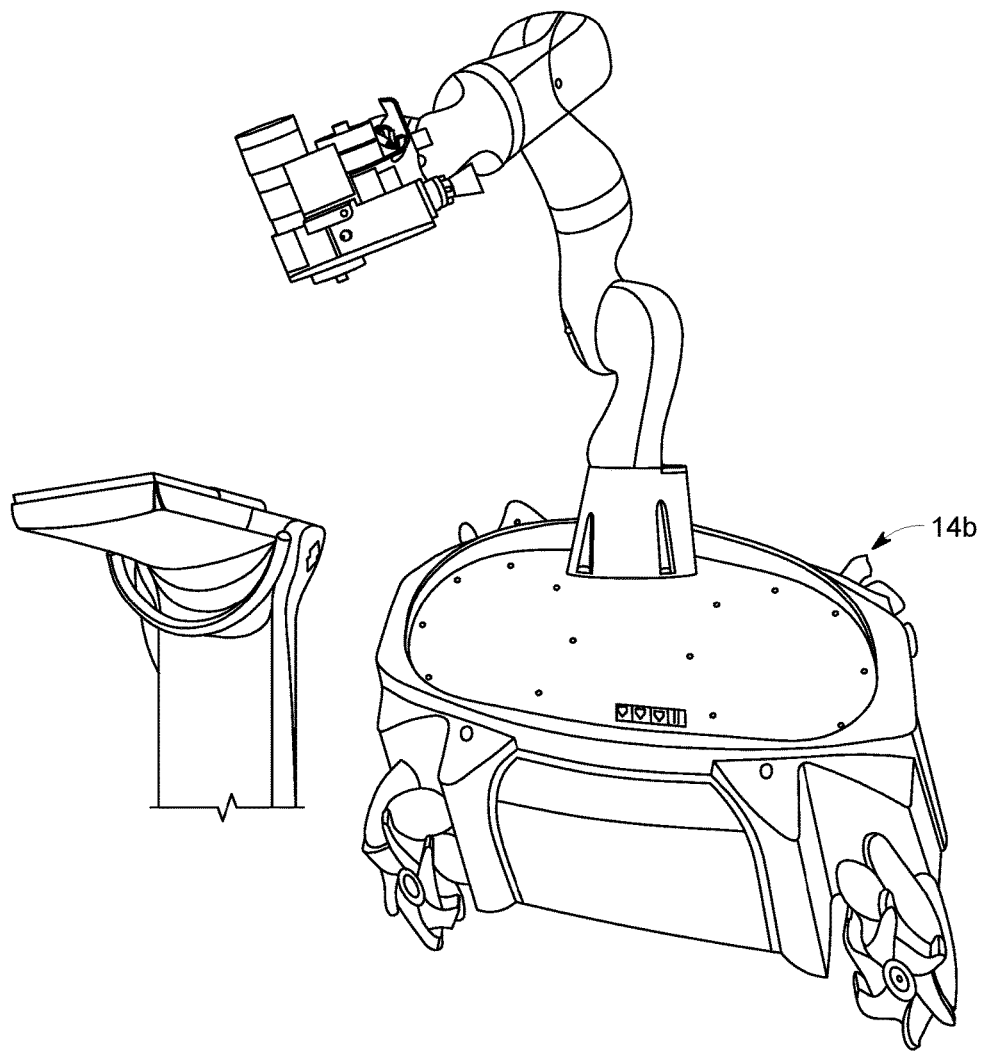
FIG. 3 is a perspective view of a mammography device according to another exemplary embodiment.

In FIG. 3 is a perspective view of a mammography device according to another exemplary embodiment, wherein the base 14 is replaced with a mobile platform 14b to which the arm 12 is fixed. The arm portions 12a, 12b, 12c are therefore arranged to move with respect to the mobile platform 14b, thus allowing supplementary degrees of freedom to position the x-ray source 2.

Figure 4:
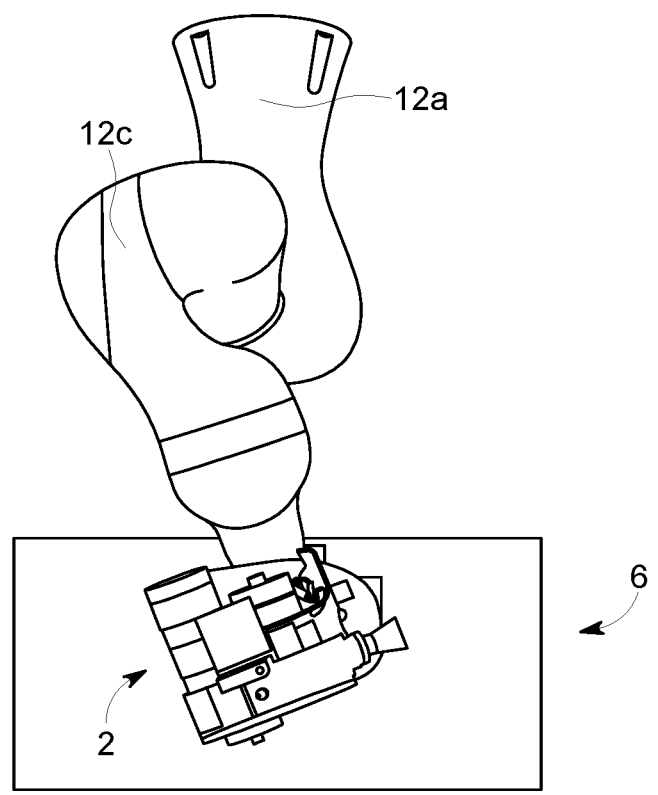
FIG. 4 is a top view of the mammography device of FIG. 1.

In FIG. 4 is shown a top view of the same device of FIG. 1, in which the x-ray source 2 is placed above the breast support plate 6.

Figure 5:
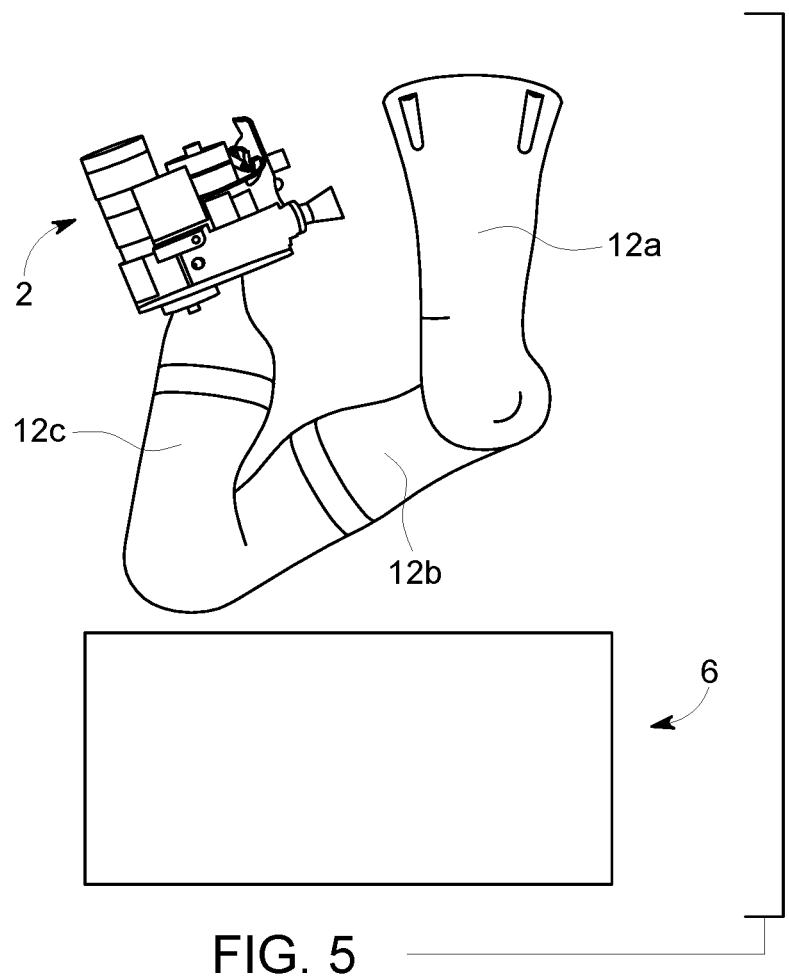
FIG. 5 is a top view of the mammography device of FIG. 1 in a parking position.
Figure 6:
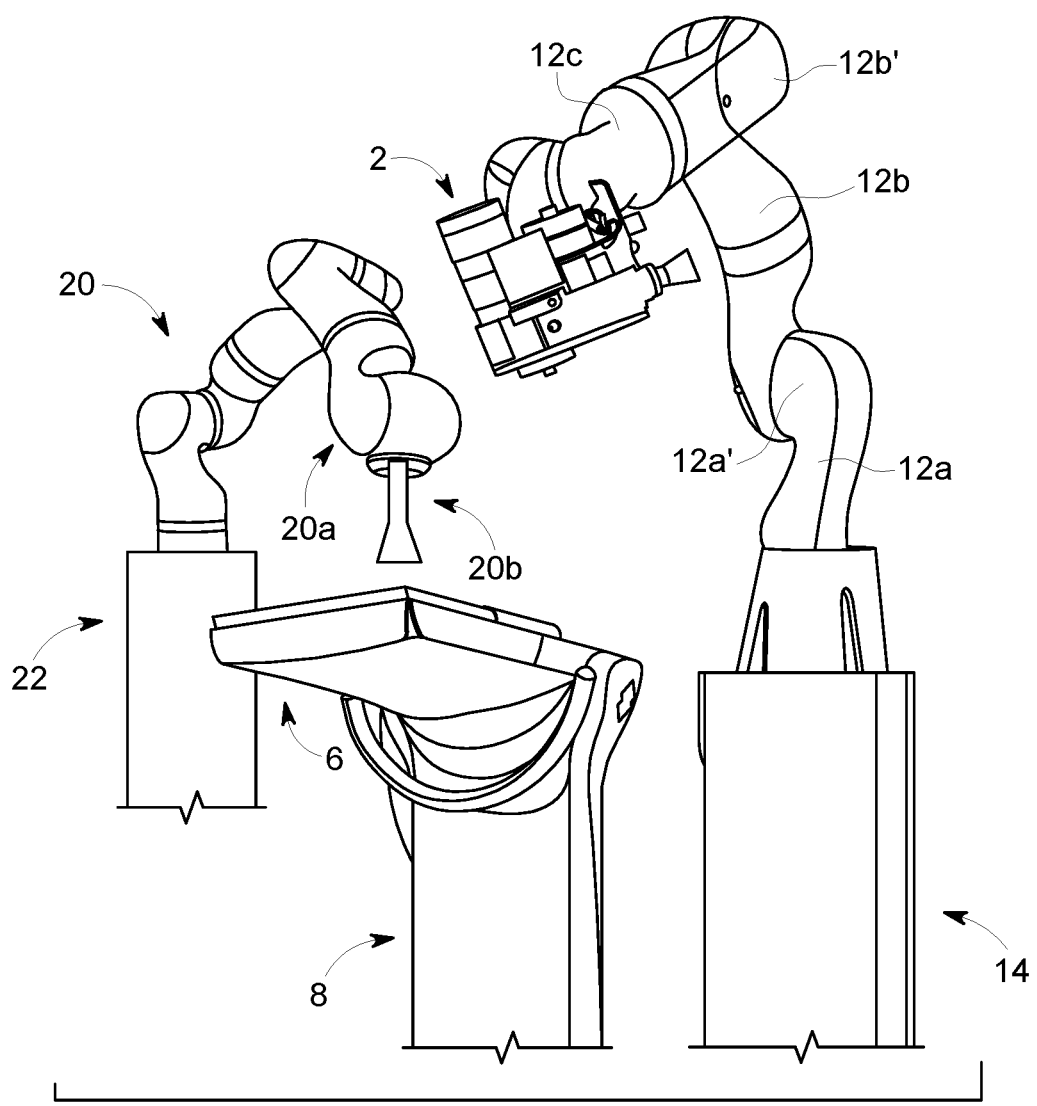
FIG. 6 is a perspective view of a mammography device, which may be used in a method for performing mammography according to another exemplary embodiment.

In FIG. 5 is shown a top view of the device of FIG. 1 wherein the arm 12 is placed in a parking position completely removed from the breast support plate 6, so that the x-ray source 2 and the arm 12 don't cover the breast support plate 6 when parked, thus allowing the physician to easily reach the patient's breast on the breast support plate 6. Thanks to the fact that the x-ray source 2 is hold the cobot arm 12, the physician can place it in any desired parking position (and not only in a predefined one) gaining a lot of free working space around the breast. In FIG. 6 is shown a perspective view of an imaging device according to an alternative embodiment. In this embodiment the device 1 further comprises an auxiliary arm 20 supported by a base 22 and arranged to cooperate with the x-ray source 2 and the x-ray detector 4 to perform additional examination to mammography. The auxiliary arm 20 includes as non-limiting examples a US probe, a biopsy device, a compression system, or another interventional device that could be useful during a breast imaging procedure. The auxiliary arm 20 may include at least a first portion 20a supporting the interventional instrument 20b. In an alternative embodiment, the arm 12 is a cobot, the auxiliary arm 20 is a robot or a cobot and also the supporting element 8 is a robot or may be a cobot.

The three robots/cobots have to be synchronized and exchange data in order to avoid collisions and optimize the image acquisition. For example, the robot/cobot of the auxiliary arm 20 sends its position to the robot/cobot of the supporting element 8, so that a control unit (not shown in the figures) associated in a manner per se known to all the robots/cobots calculates the optimal collision-free trajectory for the arm 12, in order to get the best image quality by minimizing artifacts of the images and by reducing zones hidden by the other components of the device 1. Similarly, the robot of the auxiliary arm 20 can adapt its position and orientation to the trajectory performed by the arm 12.

Thanks to the collaboration between multiple robots/cobots, the imaging trajectories of the x-ray source 2 and the auxiliary arm 20 can be optimized, maximizing the usable part of the images to perform additional interventional steps on the patient's breast such as for example a biopsy or an echography.

In another embodiment of the present disclosure, the first portion 20a of the auxiliary arm 20 is arranged to be repositionable with respect to the interventional instruments 20b, thus maximizing the usable part of the device 1.

Figure 7:
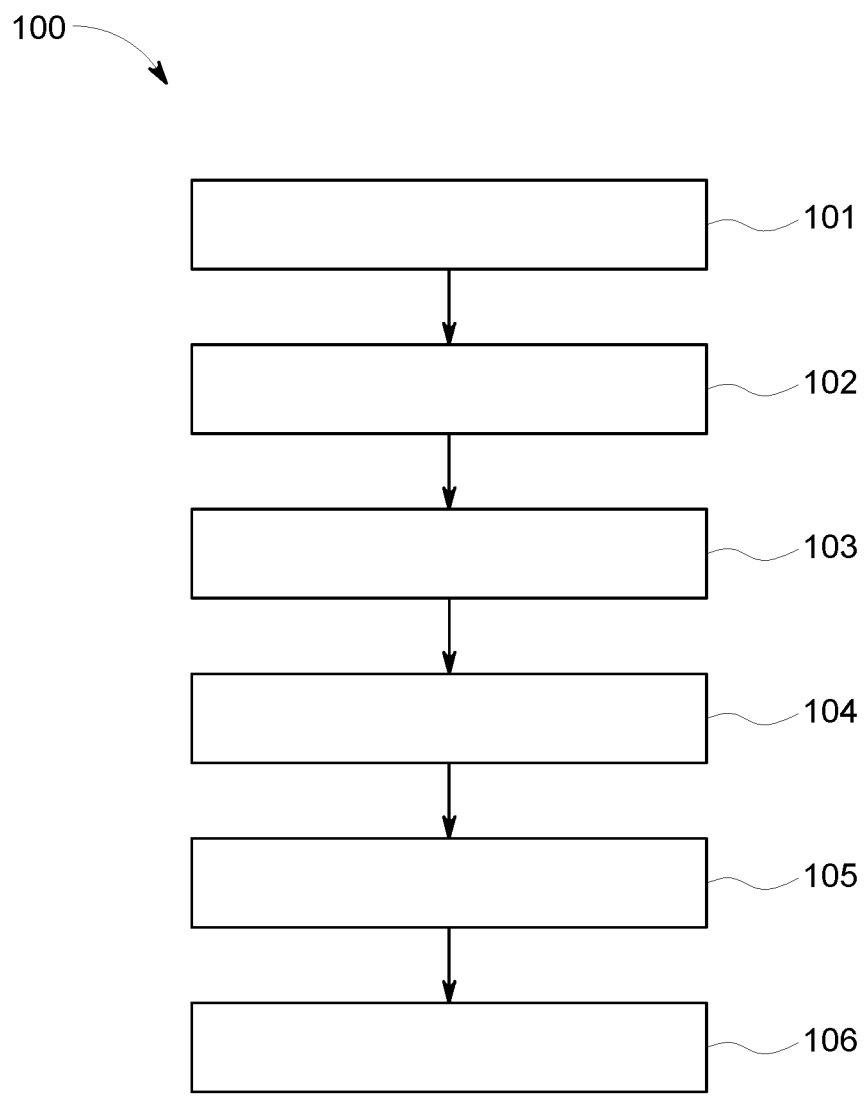
FIG. 7 shows a flow chart of a method for performing mammography.

FIG. 7 shows a flow chart according to a method 100 for performing mammography (e.g. a mammography examination or procedure) using a mammography device 1. The device comprises an x-ray source 2, an x-ray detector 4 placed under a breast support plate 6 for supporting a patient's breast and arranged to detect the x-rays coming from the x-ray source 2 after they have passed through the patient's breast, and a positioning assembly 10 for positioning the x-ray source 2 with respect to the breast support plate 6, said assembly comprising a collaborative robot arm 12. The method comprises at least the following steps. According to a first method step 101, a patient's breast is placed on the breast support plate 6. In method step 102 the x-ray source 2 is placed in a first position by moving arm portions 12a, 12b, 12c of the arm 12 through mechanical joints 12a', 12b' connecting such arm portions 12a, 12b, 12c, thus obtaining a collaborative guide and/or redirection of the motions. In method step 103 the x-ray source 2 is activated and the x-ray detector 6 detects the x-rays coming from the x-ray source 2 after they have passed through the patient's breast, thus obtaining a set of x-ray images.

In the present description, by the expression "collaborative guide and/or redirection of the motions" it is defined as follows. Because the arm 12 is a collaborative robot arm, when its portions 12a, 12b, 12c are moved they can each collaborate with the source of the motion so as to adjust it. The cobot arm portions 12a, 12b, 12c guide, redirect and/or steer motions that originate with an operator, human or otherwise, when the operator places the x-ray source 2 in the first position. Thus, both the cobot arm 12 and the operator apply forces on the x-ray source 2, with the cobot arm 12 "guessing" and/or "interpreting" the desired motions (rotations, translation, etc.) of the operator. The cobot arm portions 12a, 12b, 12c use variable transmission elements whose transmission ratios are adjustable under computer control by use of small steering motors.

Moreover, the method may further comprise an additional step 104 of placing the x-ray source in second positions by moving arm portions 12a, 12b, 12c of the arm 12 through mechanical joints 12a', 12b' connecting such arm portions 12a, 12b, 12c, thus obtaining a collaborative guide and/or redirection of the motions.

The first position may be the parking position, as previously disclosed with reference to FIG. 5, while the second position is an initial position of the imaging trajectory of the x-ray source 2, which may be any position above the breast or in any case related to the examination and the acquisition of the images, for example right or left to the breast or another parking position.

Moreover the method may further comprise an additional step 105 of moving an auxiliary robot or cobot arm 20 above the breast to perform an additional examination such as, for example, a biopsy or an echography.

Moreover the method may further comprise an additional step 106 of moving an auxiliary robot or cobot supporting element 8 supporting the breast support plate 6.

Figure 8:
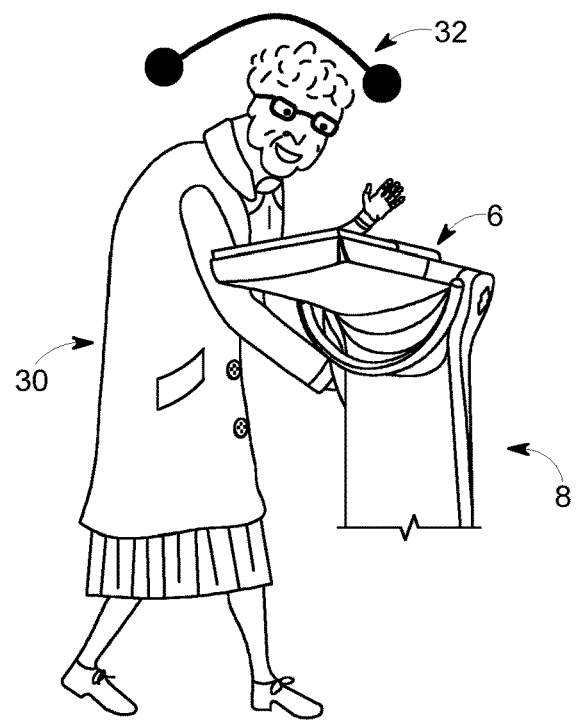
FIG. 8 shows a patient placed near the breast support plate of the device of FIG. 1 and the trajectory followed by the x-ray source according to the prior art.

In FIG. 8 is shown a patient 30 placed near the support plate 6 and a trajectory 32 that is followed by the x-ray source when applying prior art methods for performing an imaging procedure such as mammography. In well-known prior art imaging devices such as mammographs, as shown for example in FIG. 9, there is an x-ray source 50 supported by a gantry 51, which is an arm mechanically linked with a console 52 supporting the x-ray detector 54. The console 52 comprises a breast support plate 56 and the x-ray detector 54 is placed under the breast support plate 56. The gantry 51 can rotate around an axis, about a pivot joining it to the console 52, so that the x-ray source 50 moves above the x-ray detector 54 along a trajectory 32 lying in a plane 33 perpendicular to the surface of the breast support plate 56, as shown in FIG. 10. The trajectory 32 is fixed, may be arc-shaped, and determined by the mechanical link between the console 52 and the arm 51 supporting the x-ray source 50. The arm 51 is a rigid element that makes the x-ray source 50 move along a curvilinear axis 58 (see FIG. 9), which may be arc-shaped, for a predetermined length. The arm 51 is pivotally connected, at one end thereof, to the console 52, and the x-ray source 50 is placed at the other end of the arm 51. Therefore, when the arm 51 pivots, the x-ray source 50 can only move along the fixed trajectory 32.

The trajectory 32 has a starting point 32a, which correspond to the initial position of the x-ray source 50 before that the arm 51 starts to pivot, and an ending point 32b, which correspond to the final position of the x-ray source 50 when the mammography examination or procedure is finished and the arm 51 has terminated its rotation about the pivot.

Returning now to FIG. 8, it is clear that the patient 30 in certain positions may hide or obstruct a portion of the x-ray detector 4 and may also hide or obstruct a portion of her own breast (object of interest) because her head and shoulder areas are generally positioned directly above her breast. When acquiring images using the x-ray source 50 moving along the trajectory 32, the collision risk between the x-ray source 50 and the patient is high, therefore image acquisition may not be possible. To free the space above her breast to enable image acquisition, the patient has to straighten her back in an unnatural and uncomfortable manner.

Figure 11:
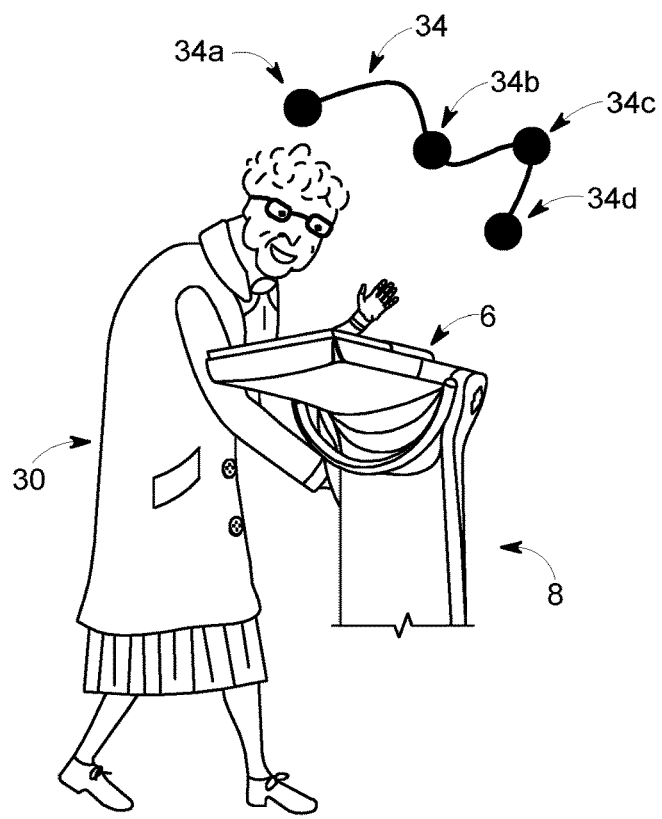
FIG. 11 shows a patient placed near the breast support plate of the device of FIG. 1 and the trajectory followed by the x-ray source according to an embodiment.

In FIG. 11 is shown the patient 30 placed near the support plate 6 of the mammography device of FIG. 1 and a non-planar trajectory 34 having at least a starting point 34a, a first intermediate point 34b, a second intermediate point 34c and an ending point 34d, such trajectory 34 being followed by the x-ray source 2 when applying the method according to embodiments. The at least four points of the trajectory 34 are non-planar. Each portion of the trajectory 34, i.e. a first portion between the starting point 34a and the first intermediate point 34b, a second portion between the first intermediate point 34b and the second intermediate point 34c, and a third portion between the second intermediate point 34c and the ending point 34d are non-planar. Alternatively, the first, second and third portions between two consecutive points of the trajectory 34 are planar but the trajectory points 34a, 34b, 34c and 34d are non-planar. The x-ray source 2 moves independently from the breast support plate 6 along a curvilinear non-planar trajectory, thus allowing the x-ray source 2 to avoid collision risks with the patient herself.

Figure 12:
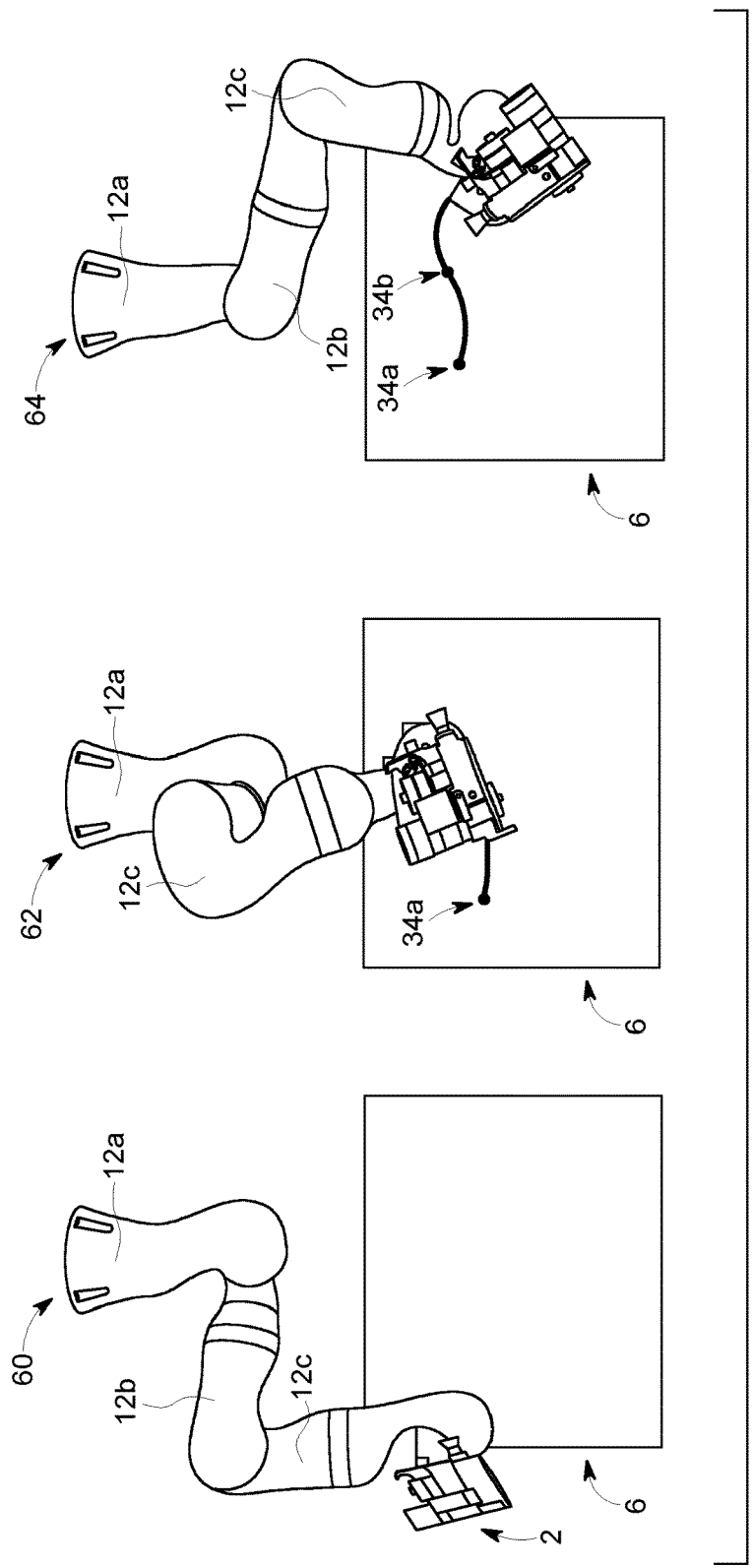
FIG. 12 is a top view of the device of FIG. 1 with the arm in three different positions.

In FIG. 12 is shown a top view of the imaging device of FIG. 1 in which the arm 12 is depicted in three consecutive positions: in a first position 60 the arm 12 places the x-ray source 2 in the starting point 34a of the trajectory 34, then the arm 12 moves in a second position 62, corresponding to the first intermediate point 34b of the trajectory 34, and finally the arm 12 moves in a third position 64, corresponding either to the second intermediate point 34c of the trajectory 34 or to the ending point 34d of the trajectory 34.

The arm 12 is initially moved by the physician and then it automatically continues, guides, modifies and/or redirects the movement so as to complete it according to the desires of the physician. Thanks to the fat that the arm 12 is a collaborative robot arm, when its portions 12a, 12b, 12c are moved they can each collaborate with the source of the motion (the manual one) so as to adjust it. The cobot arm portions 12a, 12b, 12c guide, redirect and/or steer motions that originate with the human operator when he/she places the x-ray source 2 in the starting position 34a. Thus, both the cobot arm 12 and the human operator apply forces on the x-ray source 2, with the cobot arm 12 essentially guessing and/or interpreting the desired motions (rotations, translation, etc.) of the human operator. The cobot can also compensate for the x-ray source weight. The cobot arm portions 12a, 12b, 12c use variable transmission elements whose transmission ratios are adjustable under computer control by use of small steering motors.

Figure 9:
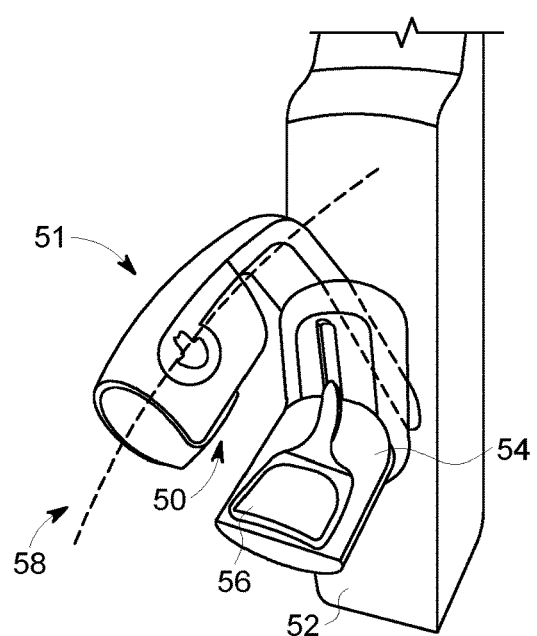
FIG. 9 is an exemplary mammography device.
Figure 10:
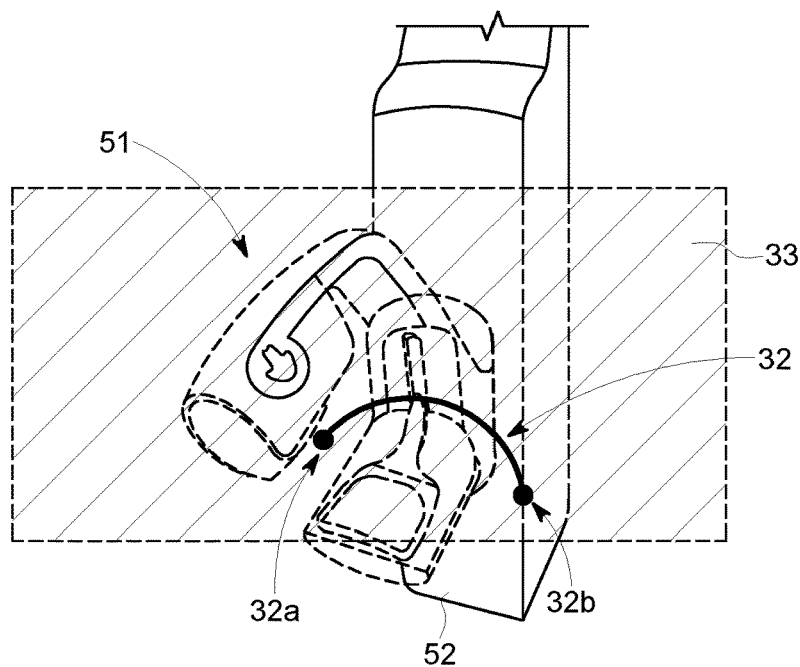
FIG. 10 is a front view of the plane on which lies the trajectory followed by the x-ray source of the mammography device of FIG. 9.
Figure 13:
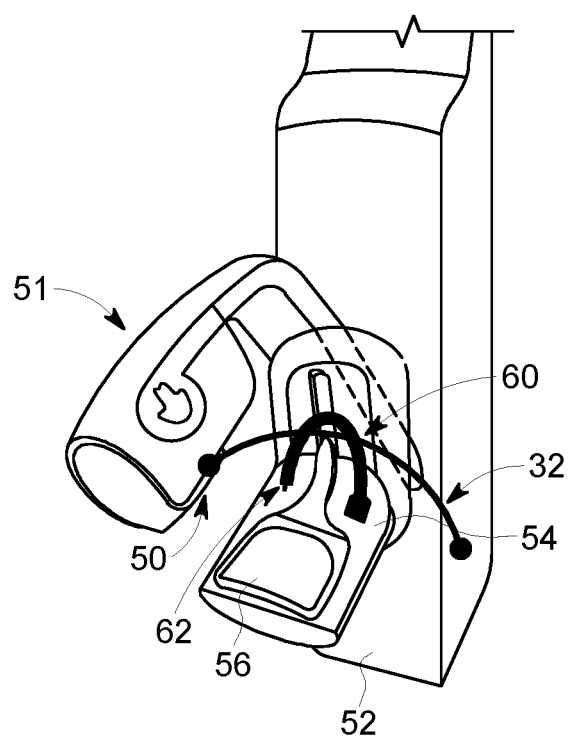
FIG. 13 shows the prior art mammograph device of FIG. 9 provided with an auxiliary interventional device.

In FIG. 13 is shown the prior art imaging device of FIG. 9 provided with an auxiliary interventional device 60, such as for example a biopsy positioner having a needle 62. If the needle 62 or an element of the interventional device 60 is placed on the trajectory 32 followed by the x-ray source 50, due to constructional constraints of the mammograph, the x-ray source 50 can be partially hidden or obstructed by the interventional device 60, thus resulting in poor image acquisition. In addition, a stereo control view of the acquired images or a digital breast tomosynthesis biopsy is improbable if not impossible due to likely collisions between the x-ray source 50 and the interventional device 60 (or a part thereof).

Figure 14:
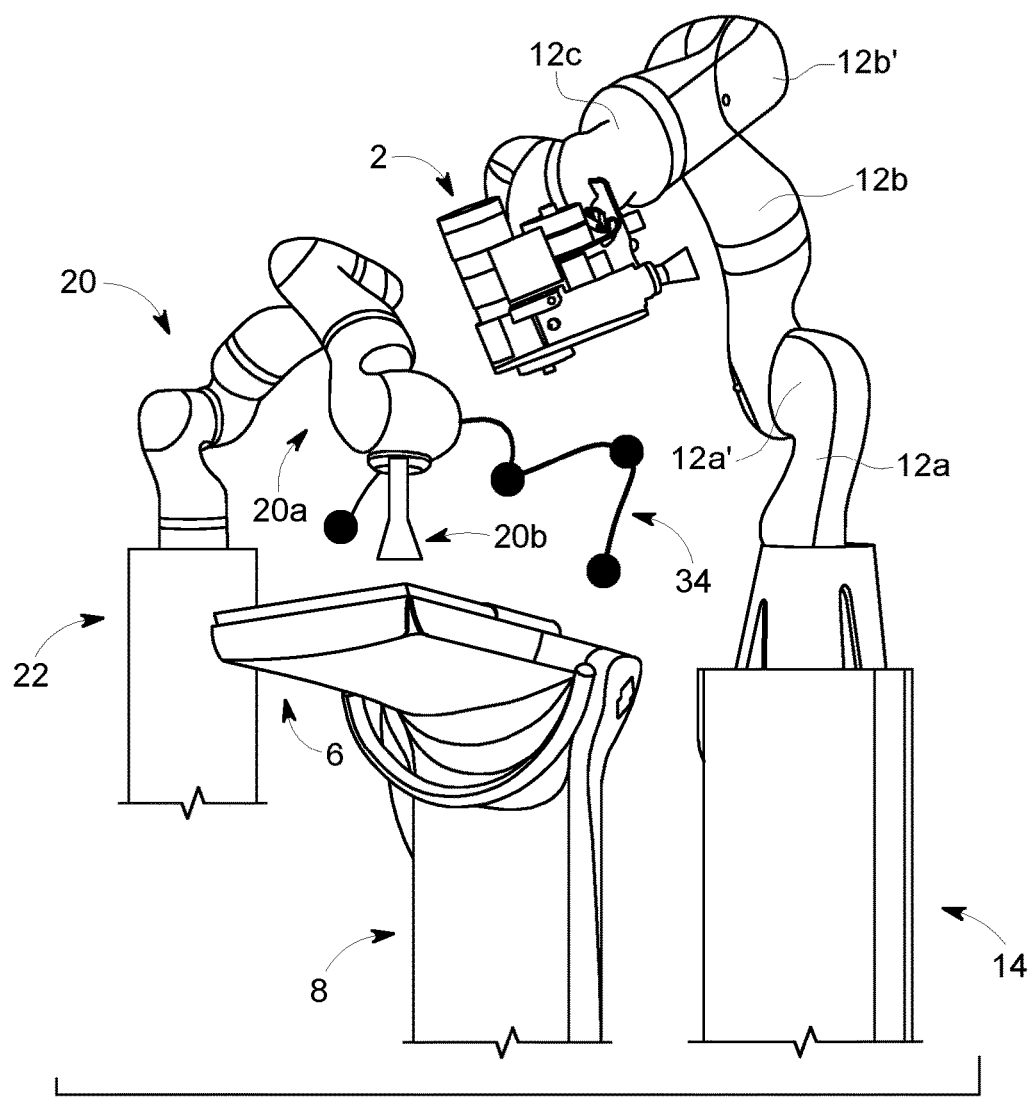
FIG. 14 shows the device of FIG. 6 and the trajectory followed by the x-ray source according to an embodiment.

In FIG. 14 is shown the imaging device of FIG. 6 and the trajectory 34 followed by the x-ray source 2 according to an embodiment. It is evident that the x-ray source 2 can be moved independently from the auxiliary arm supporting the interventional device 20b, thus avoiding collisions between the two devices. The x-ray source 2 can move around the interventional device 20b, thus allowing safer image acquisition and improvement of the image quality of the acquired images and optimization of the method for performing breast imagining procedures, due to minimization of the part of the x-ray detector 4 hidden by the interventional device 20b.

Alternatively, the auxiliary arm can be moved around the x-ray source 2 along a non-planar trajectory as disclosed above, so that the interventional device 20b does not hit the x-ray source 2.

Figure 15:
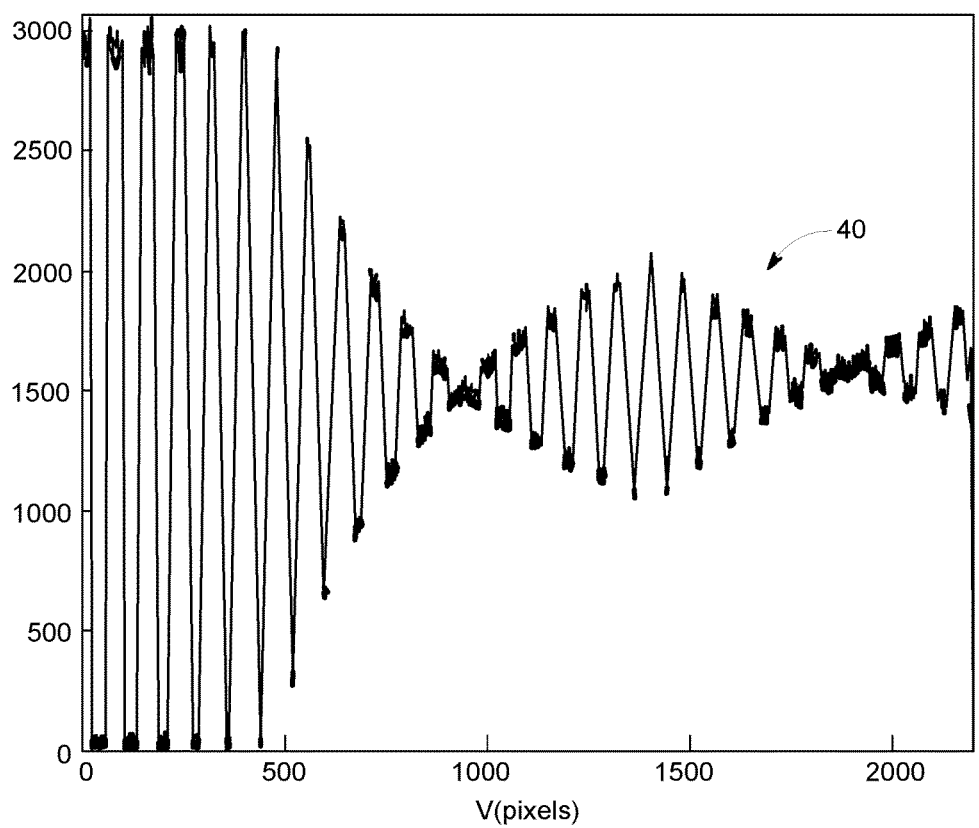
FIG. 15 is a signal reconstructed after detection from an x-ray detector when applying a method according to the prior art.

With reference to FIG. 15, a signal reconstructed after detection from an x-ray detector when applying a method according to the prior art is generally indicated 40. The signal 40 is obtained by applying, using the mammography device of FIG. 9, a test on a Defrise phantom, wherein a plurality of samples of an x-ray signal coming from the x-ray source 50 are collected by the x-ray detector 54 when the x-ray source 50 moves above the phantom along the arc-shaped trajectory 32. The signal 40 is reconstructed from the x-ray detector 54 after receiving the original x-ray beam coming from the x-ray source 50. The signal level (y axis of the graph of FIG. 15) is depicted as a function of the distance to the chest wall, and the unit is the pixel of the image acquired by the mammograph. The signal quality degrades rapidly when going away from the chest wall.

Figure 16:
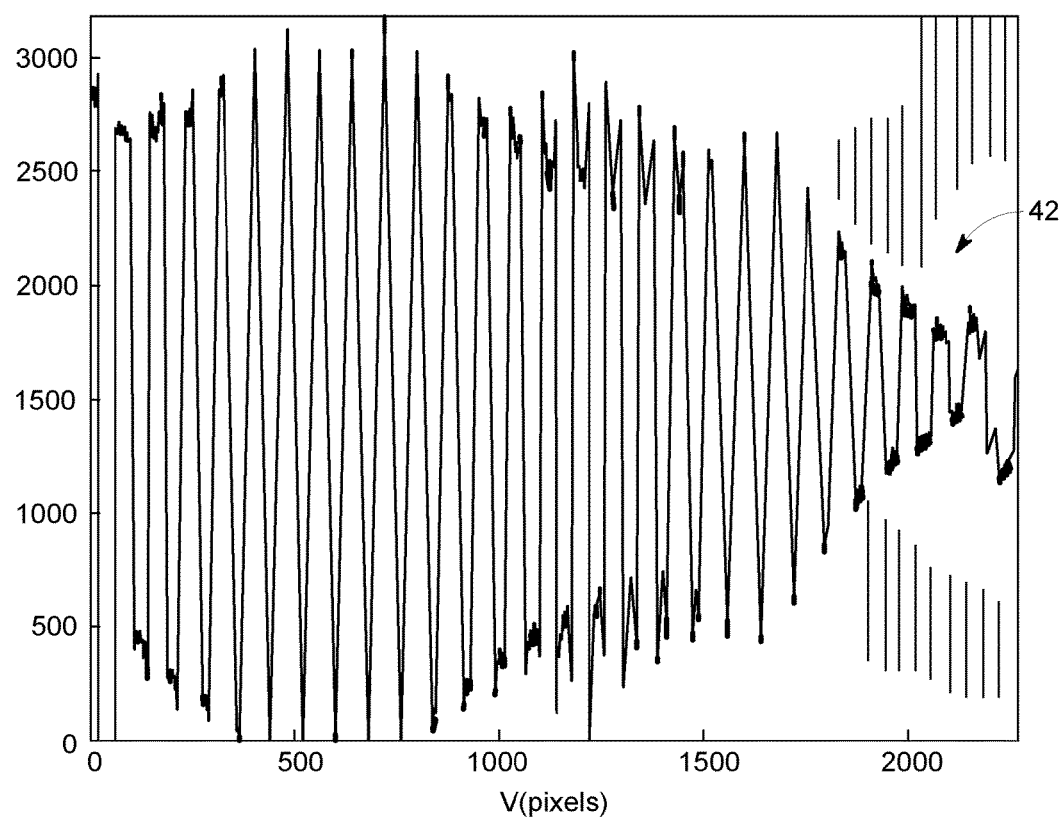
FIG. 16 is a signal reconstructed after detection from an x-ray detector when applying a method according to an embodiment.

In FIG. 16 is shown a signal 42 reconstructed after detection from an x-ray detector when applying a method according to an embodiment. The signal 42 is obtained by applying, using the mammography device of FIG. 1, a test on a Defrise phantom, wherein a plurality of samples of the x-ray signal coming from the x-ray source 2 are collected by the x-ray detector 4 when the x-ray source 2 moves above the phantom along the zig-zag trajectory 34. The profile of the signal 42 detected by the x-ray detector 4 and corresponding to the original x-ray beam sent by the x-ray source 2 is better reconstructed with respect to the profile of the signal 40 depicted in FIG. 15. With the expression "better reconstructed" it is meant that the detected signal better and more uniformly matches the original phantom signal.

Figure 17:
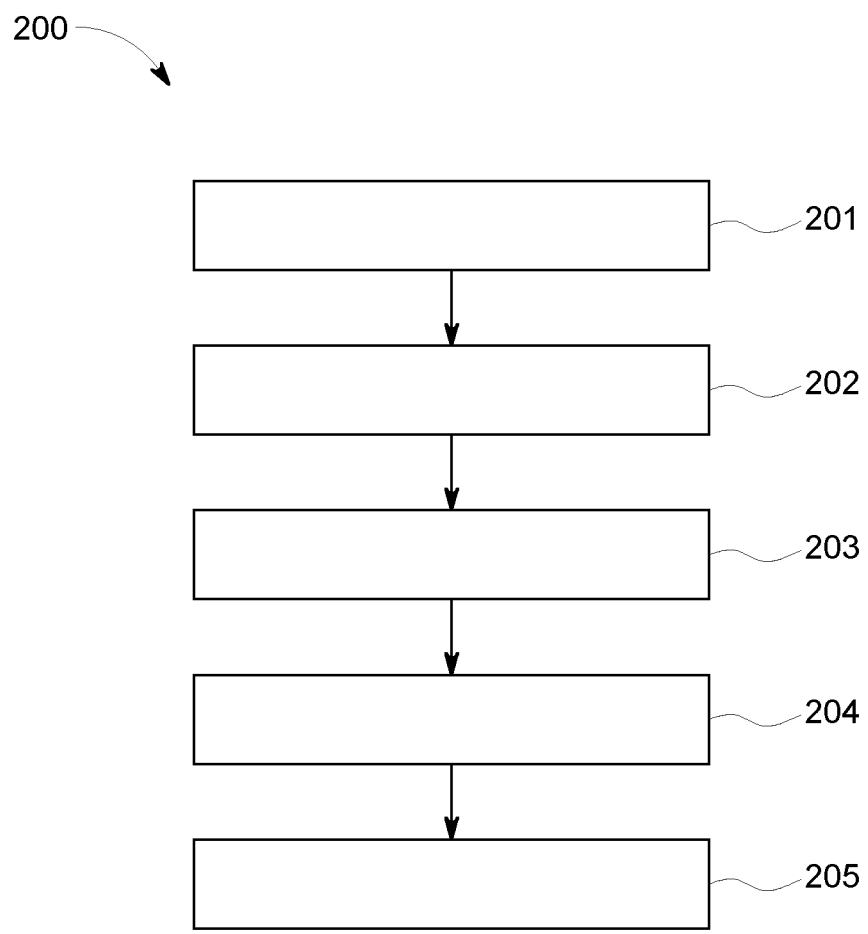
FIG. 17 shows a flow chart of a method for performing mammography according to an exemplary embodiment.

FIG. 17 shows a flow chart according to an embodiment of a method 200 for performing an imaging procedure using a device 1. As indicated above, the device 1 comprises an x-ray source 2, an x-ray detector 4 placed under a support plate 6 for supporting an object of interest, in particular a patient's breast, and arranged to detect the x-rays coming from the x-ray source 2 after they have passed through the object of interest, and a positioning assembly 10 for positioning the x-ray source 2 with respect to the support plate 6 comprising a collaborative robot arm 12. Said method comprises at least the steps set forth following.

According to a first method step 201 an object of interest is placed on the support plate 6. In method step 202 the x-ray source 2 is moved along a non-planar trajectory. In method step 203 the x-ray source 2 is activated and the x-ray detector 4 detects the object of interest, thus obtaining a set of x-ray images.

In method step 204 the arm portions 12a, 12b, 12c of the arm 12 are rotated and/or translated through the mechanical joints 12a', 12b' connecting such arm portions 12a, 12b, 12c to be controlled, thus obtaining collaborative guides and/or redirection of the motions. In method step 205 the auxiliary arm 20 is moved along a non-planar trajectory above the object of interest, to perform an additional examination such as, for example, a biopsy or an echography.

In method step 206 the x-ray source 2 is moved along a non-planar trajectory computed by taking into account the environment and the patient position, and/or the biopsy device position, and/or the auxiliary arm 20 position, and/or a priori/pre-exam/per-exam information. The x-ray source may be dynamically moved. The dynamically movement refers, in particular, to the fact that the trajectory of the x-ray source 2 is updated during the examination according to the patient's movements, the changes of the environment, etc. If the patient moves during the image acquisition, the arm 12 automatically adapts the trajectory of the x-ray source 2 to the new patient position. In each time instant the computer of the arm 12 calculates the optimal trajectory for the x-ray source 2 taking into account the position of the patient in the previous time instant, the movement of the patient, the presence of obstacles in the environment, etc.

Thanks to the fact that non-planar trajectories are followed when applying the method according to an embodiment, the image quality increases and also the capability to adapt the trajectory to the actual patient position and/or to the environment around the patient and/or per-exam information is improved. In this way, x-ray artefacts of the images are avoided; the final examination can be also adapted to a priori and/or pre-exam and/or per-exam information on the object to image and the position of the patient can be natural and ergonomic.

This description uses examples to disclose the methods, systems, and apparatuses, including the best mode, and also to enable any person skilled in the art to practice the teachings described herein, including making and using any devices or systems and performing any incorporated methods. The patentable scope of the disclosure is defined by the claims, and may include other examples that occur to those skilled in the art.

What is claimed is:

1. A mammography device comprising:
    an x-ray source;
    an x-ray detector placed under a breast support plate for supporting a patient's breast and being arranged to detect the x-rays coming from the x-ray source after they have passed through the patient's breast; and
    a positioning assembly for positioning the x-ray source with respect to the breast support plate, the positioning assembly comprising an arm having multiple degrees of freedom to move the x-ray source relative to the patient's breast along a non-planar trajectory extending in a tridimensional space and not lying in a plane such that each portion of the trajectory between two consecutive points is non-planar, said arm being a collaborative robot or cobot.

2. The device according to claim 1, wherein the arm comprises a plurality of arm portions connected each to other in respective joints, so that each arm portion can at least one of translate and rotate with respect to its adjacent arm portions.

3. The device according to claim 2, wherein the arm is supported on at least one of a column and platform, said platform being fixed or mobile, enabling the arm to translate in at least one of a vertical and horizontal direction.

4. The device according claim 3, further comprising at least one supporting element for supporting the breast support plate and the x-ray detector, wherein the at least one supporting element is mechanically decoupleable from the arm.

5. The device according to claim 2, further comprising an auxiliary arm arranged to cooperate with the x-ray source and the x-ray detector.

6. The device according to claim 4, wherein the at least one supporting element is a robot or cobot.

7. A method for performing a mammography by a device comprising an x-ray source, an x-ray detector placed under a breast support plate for supporting a patient's breast and arranged to detect the x-rays coming from the x-ray source after they have passed through the patient's breast, and a positioning assembly having multiple degrees of freedom for positioning the x-ray source with respect to the breast support plate comprising a collaborative robot arm, the method comprising:
    placing a patient's breast on the breast support plate;
    placing the x-ray source in a first position by moving arm portions of the arm through mechanical joints connecting such arm portions, said arm being controlled so as to obtain collaborative guides and/or redirection of the motions;
    via the positioning assembly, moving the x-ray source relative to a patient's breast along a non-planar trajectory, wherein the non-planar trajectory extends in a tridimensional space not lying in a plane such that each portion of the trajectory between two consecutive points is non-planar.

8. The method according to claim 7, wherein the trajectory comprises at least a starting point corresponding to the first position, a first intermediate point corresponding to a second position, and a second intermediate point or an ending point corresponding to a third position.

9. The method according to claim 7, further comprising performing an additional examination, said performing including moving an auxiliary robot arm or cobot arm to aid in performing the an additional examination, the additional examination being a biopsy or an echography.

10. A method for performing an imaging procedure using an imaging device comprising an x-ray source, an x-ray detector placed under a support plate for supporting an object of interest and arranged to detect the x-rays coming from the x-ray source after they have passed through the object of interest, and a positioning assembly having multiple degrees of freedom for positioning the x-ray source with respect to the support plate comprising an arm, the method comprising:
    placing an object of interest on the support plate;
    moving the x-ray source relative with the object of interest along a non-planar trajectory;
    activating the x-ray source and the x-ray detector so as to detect the x-rays coming from the x-ray source after they have passed through the object of interest, thus obtaining a set of x-ray images, wherein the non-planar trajectory extends in a tridimensional space not lying in a plane such that each portion of the trajectory between two consecutive points is non-planar.

11. The method according to claim 10, wherein the trajectory comprises at least a starting point, a next first intermediate point, a next second intermediate point and a next ending point.

12. The method according to claim 10, wherein the x-ray source is moved by rotating and/or translating arm portions of the arm through mechanical joints connecting such arm portions to be controlled, so as to obtain collaborative guides and/or redirection of the motions of the x-ray source.

13. The method according to claim 12, further comprising moving the x-ray source along a non-planar trajectory so as to avoid collision with an interventional device associated with the imaging device.

14. The method according to claim 13, further comprising moving the interventional device along a non-planar trajectory above the object of interest so as to avoid collision between the interventional device and the x-ray source.

15. The method according to claim 10, wherein the x-ray source is moved along a non-planar trajectory computed by taking into account the environment, patient position, and, if a biopsy device is present, the position of the biopsy device.

16. An imaging device for acquiring images of an object of interest, comprising
an x-ray source;
an x-ray detector placed under a support plate for supporting an object of interest and arranged to detect the x-rays coming from the x-ray source after they have passed through object of interest;
an arm supporting the x-ray source, said arm defining multiple arm segments enabling multiple degree of freedom movements between points, and wherein the x-ray source is movable by rotating and/or translating arm segments via mechanical joints connecting such arm segments, so as to obtain collaborative guides and/or redirection of the motions of the x-ray source,
wherein the x-ray source is movable relative to the object of interest along a non-planar trajectory extending in a tridimensional space and not lying in a plane such that each portion of the trajectory between two consecutive points is non-planar.

17. The device according to claim 16, wherein the trajectory comprises at least a starting point, a next first intermediate point, a next second intermediate point and a next ending point.

18. The device according to claim 16, wherein the x-ray source is movable along a non-planar trajectory so as to avoid collision with an interventional device associated to the imaging device.

19. The device according to claim 1, wherein the trajectory comprises at least a starting point, a next first intermediate point, a next second intermediate point and a next ending point.

* * * * *